Oct. 5, 1971 R. V. LINDQUIST Plant Pat. 3,063
ROSE PLANT
Filed July 11, 1969
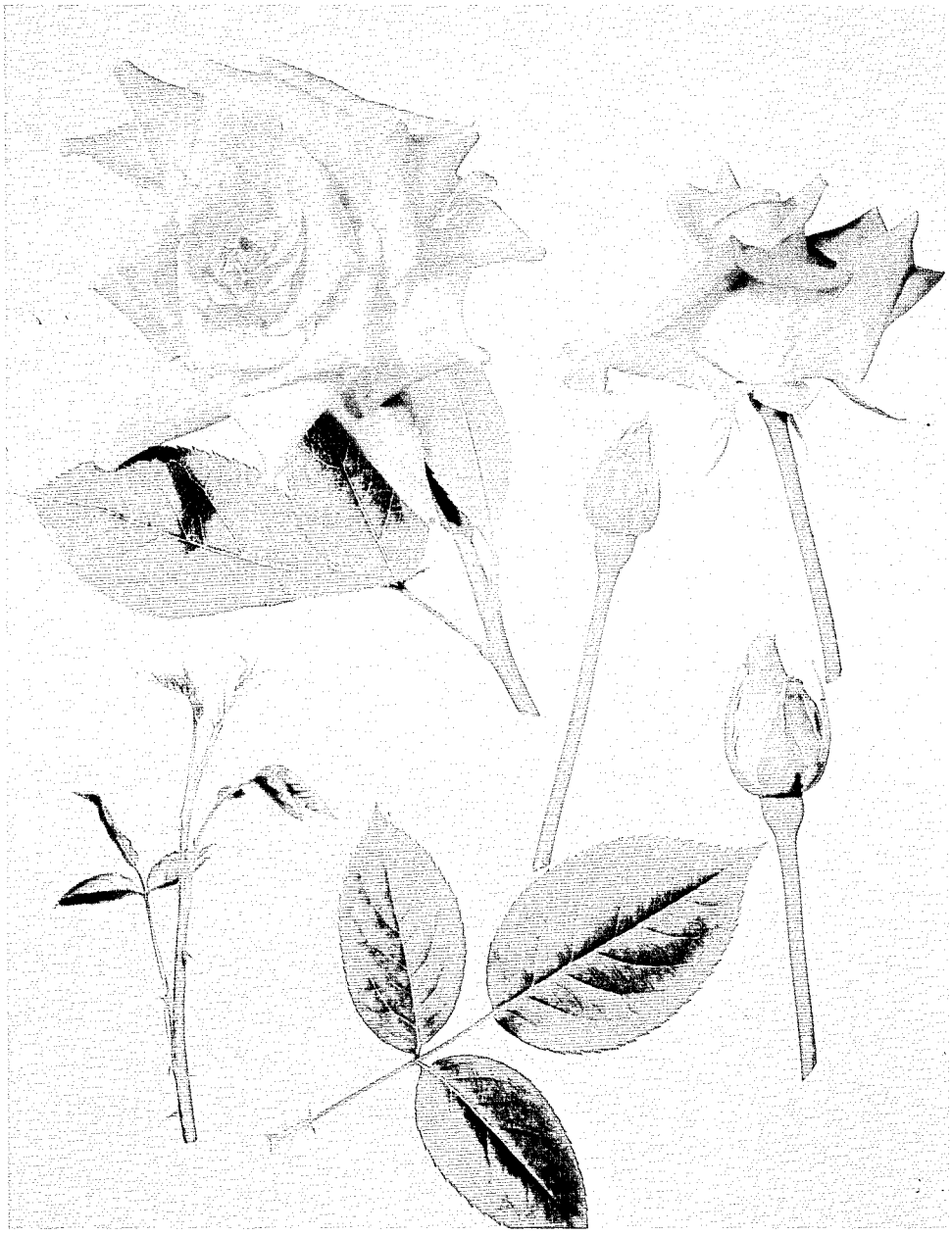
Inventor.
R. V. Lindquist
By: Robb & Robb
Attorneys.

United States Patent Office

Plant Pat. 3,063
Patented Oct. 5, 1971

3,063
ROSE PLANT

Robert V. Lindquist, Hemet, Calif., assignor to Hemet Wholesale, Hemet, Calif.

Filed July 11, 1969, Ser. No. 841,157
Int. Cl. A01h 5/00
U.S. Cl. Plt.—17 1 Claim The present invention relates to a new and distinct variety of rose plant of the hybrid tea class, which was originated by me by crossing the rose variety known as "Tropicana" (Plant Patent No. 1,969) with the rose variety known as "Hawaii" (Plant Patent No. 1,833), the former being the seed parent and the latter being the pollen parent.

As the result of this breeding, I have produced a new and improved rose variety which is particularly characterized as to novelty by the following unique combination of features which are outstanding therein and which distinguish it from its parents, as well as from all other rose varieties of which I am aware:

(1) A vigorous and upright habit of growth;
(2) A unique, star-shaped flower form;
(3) Better than average flower petal substance; and
(4) A distinctive and attractive bright coral orange flower color.

Asexual reproduction of the new variety by budding, as performed at Hemet, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new rose variety, with color terminology in accordance with the Royal Horticultural Colour Chart, published by the Royal Horticultural Society of London:

Type: Hardy; tall; bush; outdoor; seedling; for cut flowers and for garden decoration.
Class: Hybrid tea.
Breeding: Seedling.
*Seed parent.*—"Tropicana."
*Pollen parent.*—"Hawaii."
Propagation: Holds its distinguishing characteristics through succeeding propagations by budding.

*Flower*

Locality where grown and observed: Hemet, Calif.
Flowers borne: Usually singly, but sometimes two or three to stem; on strong, long stems.
Quantity of bloom: Free, both outdoors and in greenhouse.
Continuity: Continuous during growing season.
Fragrance: Strong.
*Nature.*—Fruity.

Bud:
*Peduncle.*—Average length; average caliper; erect; moderately smooth; some gland-tipped cilia; few prickles. Color—Near Yellow-Green, Group 146B.
*Before calyx breaks.*—Size—Medium. Form—Medium length; pointed ovoid; with a conspicuous neck; with foliaceous appendages and gland-tipped cilia on the surface of the bud; usually with slender, bristle-like foliaceous parts extending beyond the tip of the bud.

*Ascalyx breaks.*—Color—Near Red, Group 45 C.
*Sepals.*—Lined with gland-tipped cilia and hairs. Inner surface—with fine, wooly tomentum. Margins—some have foliaceous appendages numbering from 5 to 7.
*As first petal opens.*—Size—average. Form—medium length; pointed. Color—Outside—Near Red, Group 43 C, with small base of near Yellow, Group 11 C. Inside—Near Red, Group 40 A, with small base of near Yellow, Group 11 A.
*Opening.*—Opens up well; is not prevented from opening by hot, wet or dry weather.

Bloom:
*Size (when fully open).*—Large; from 5½ inches to 6 inches.
*Petalage.*—Double; from 25 to 35 petals, plus 4 to 6 petaloids; arranged irregularly.
*Form.*—High-centered at first, but becoming cupped to high-centered; petals being at first somewhat tightly cupped, with tips reflexed and quilled outward, but later becoming somewhat loosely cupped, with tips reflexed and quilled outward at maturity.

Petals:
*Texture.*—Medium thickness.
*Appearance.*—Inside—slightly shiny. Outside—slightly satiny.
*Shape.*—Outside—nearly round, with apex flat. Intermediate—nearly round, with apex from rounded to flat. Inside—nearly round, with apex rounded.

This description of a newly opened flower was made from a rose grown in a greenhouse during the month of May at Hemet, Calif.:

*Color.—Outher petal*—outside surface—Near Red, Group 41 C, with small base of near Yellow, Group 11 C. inside surface—Near Red, Group 41 A, with small base of near Yellow, Group 11 B. *Intermediate petal*—outside surface—Near Red, Group 41 C, with small base of near Yellow, Group 11 C. inside surface—Near Red, Group 41 A, with small base of near Yellow, Group 11 B. *Inner petal*—outside surface—Near Red, Group 43 C, with small base of near Yellow, Group 11 C. inside surface—Near Red, Group 43 A, with small base of near Yellow, Group 11 B.

This description was made from a rose that was open for three days in a greenhouse during the month of May at Hemet, Calif.:

*Color.—Outer petal*—outside surface—Near Red, Group 41 C, with base of near Yellow, Group 11 D. inside surface—Near Red, Group 41 B, with base of near Yellow, Group 11 C. *Inner petal*—outside surface—Near Red, Group 41 C, with base of near Yellow, Group 11 D. inside surface—Near Red, Group 41 B, with base of near Yellow, Group 11 C.
*General color effect.*—Newly opened flower—Bright Coral Orange. 3-days open—Pale Coral Orange.
*Behavior.*—Drop off cleanly.
*Flower longevity.*—On bush in garden—4 or 5 days in May. Cut roses grown outdoors and kept at living-room temperatures—4 or 5 days in May. Cut roses grown in greenhouse and kept at living-room temperatures—4 or 5 days in May.

*Reproductive organs*

Stamens: Average number; arranged regularly about pistils.
Filaments: From short to medium length; most with anthers.

Anthers: Medium size; all open approximately at once.
*Color.*—Upper side—Near Orange, Group 24 B. Under side—Near Orange, Group 24 C.
Pollen: Abundant.
*Color.*—Near Orange, Group 24 A.
Pistils: Average number (approximately 125).
Styles: Uneven; from short to average length; thin; somewhat bunched.
Stigma:
*Color.*—Near Orange, Group 25 A.
Ovaries: Usually most enclosed in calyx.
Hips: Average length; pear-shaped; smooth; walls thin and fleshy.
*Color.*—Near Orange-Red, Group 31 A.
Sepals: Falling soon; medium length; spear-shaped; recurved.
*Color.*—Inside—Near Yellow-Green, Group 147 C. Outside—Near Yellow-Green, Group 146 B.
Seeds: Few (from 10 to 15); usually medium size.

*Plant*

Foliage:
*Leaves.*—Compound of usually 5–7 leaflets; normal abundance; medium size; moderately heavy; somewhat leathery; semi-glossy
*Leaflets.*—Shape—oval. Apex—mucronate. Base—round. Margin—serrate.
*Color.* — Mature — Upper surface—Near Yellow-Green, Group 147 A. Under surface—Near Yellow-Green, Group 148 B. Young—Upper surface—Near Green, Group 137 A. Under surface—Near Yellow-Green, Group 148 C.
*Rachis (the supporting stem of the compound leaf).*—Average size. Upper side—grooved; with few stipitate glands on edges. Under side—moderately smooth; prickly.
*Stipules.*—Medium length; very narrow; with short points turning out at an angle of more than 45°.

*Disease resistance.*—Mildly subject to mildew, as determined by comparison with other rose varieties grown under comparable conditions at Hemet, Calif.
Growth:
*Habit.*—Upright much-branched.
*Growth.*—Very free; vigorous.
*Canes.*—From medium caliper to heavy.
*Main stems.*—Color—Near Yellow-Green, Group 146 A. Large prickles—several; from medium length to long; almost straight; with medium length, narrow base. Color—Near Brown, Group 200 D. Small prickles—several. Color—Near Brown, Group 200 D. Hairs—none.
*Branches.*—Color—Near Yellow-Green, Group 148 A. Large prickles—several; medium length; almost straight; with medium length, narrow base. Color—Near Greyed-Orange, Group 165 B. Small prickles—several. Color—Near Greyed-Orange, Group 165 B. Hairs—none.
*New shoots.*—Color—Near Greyed-Purple, Group 187 B. Large prickles—Few, medium length; almost straight; with medium length, narrow base. Color—Near Greyed-Purple, Group 181 B. Small prickles—Few. Hairs—none.

I claim:

1. A new and distinct variety of rose plant of the hybrid tea class, substantially as herein shown and described, characterized particularly as to novelty by the unique combination of a vigorous and upright habit of growth, a unique, star-shaped flower form, better than average flower petal substance, and a distinctive and attractive bright coral orange flower color.

No references cited.

ROBERT E. BAGWILL, Primary Examiner